(12) United States Patent
Gromotka et al.

(10) Patent No.: US 9,026,225 B2
(45) Date of Patent: May 5, 2015

(54) OVERVOLTAGE PROTECTION ELEMENT

(75) Inventors: Bernhard Gromotka, Berlin (DE); Dirk Mader, Berlin (DE)

(73) Assignee: BIOTRONIK CRM Patent AG (CH)

( * ) Notice: Subject to any disclaimer, the term of this patent is extended or adjusted under 35 U.S.C. 154(b) by 881 days.

(21) Appl. No.: 12/482,005

(22) Filed: Jun. 10, 2009

(65) Prior Publication Data

US 2010/0087897 A1   Apr. 8, 2010

(30) Foreign Application Priority Data

Oct. 6, 2008   (DE) .......................... 10 2008 002 330

(51) Int. Cl.
*A61N 1/08*   (2006.01)
*A61N 1/375*   (2006.01)
*A61N 1/39*   (2006.01)

(52) U.S. Cl.
CPC ........ *A61N 1/08* (2013.01); *A61N 1/375* (2013.01); *A61N 1/3931* (2013.01); *A61N 1/3968* (2013.01)

(58) Field of Classification Search
CPC ........................................................ A61N 1/08
USPC ................................. 607/63; 361/91.1, 91.6
See application file for complete search history.

(56) References Cited

U.S. PATENT DOCUMENTS

| | | | |
|---|---|---|---|
| 3,690,313 A * | 9/1972 | Weppner et al. ............... 600/508 |
| 4,440,172 A | 4/1984 | Langer | |
| 4,595,009 A | 6/1986 | Leinders | |
| 4,661,979 A | 4/1987 | Jakab | |
| 4,745,923 A * | 5/1988 | Winstrom ........................ 607/9 |
| 4,796,630 A | 1/1989 | Regna | |
| 4,830,006 A * | 5/1989 | Haluska et al. ................... 607/4 |
| 5,170,806 A | 12/1992 | Colen | |
| 5,751,531 A | 5/1998 | Rault | |
| 5,833,710 A | 11/1998 | Jacobsen | |
| 2003/0163170 A1 * | 8/2003 | Faisandier ..................... 607/27 |
| 2007/0049993 A1 | 3/2007 | Hofmann et al. | |
| 2009/0132007 A1 | 5/2009 | Snitting | |

FOREIGN PATENT DOCUMENTS

| | | |
|---|---|---|
| DE | 10 2006 033925 A1 | 1/2008 |
| EP | 0 426 969 A | 5/1991 |
| WO | WO 2006/057587 A | 6/2006 |

OTHER PUBLICATIONS

European Search Report of Oct. 8, 2009 for corresponding EP 09159865.

* cited by examiner

*Primary Examiner* — Alyssa M Alter
(74) *Attorney, Agent, or Firm* — Craig A. Fieschko, Esq.; DeWitt Ross & Stevens S.C.

(57) ABSTRACT

An overvoltage protection element, provided as a component of a medical device (3) used on or in a human or animal body, reduces power absorption upon application of an external overvoltage signal having chronological rising and/or decay characteristic at an interface (15) of the medical device (3). The overvoltage protection element has reshaping means (17) which convert the external overvoltage signal at the interface (15) into an internal voltage pulse, and limiting means (19) which limit a voltage drop on at least one electronic component of the medical device to a predetermined limiting value.

22 Claims, 3 Drawing Sheets

OVERVOLTAGE PROTECTION ELEMENT

FIELD OF THE INVENTION

The invention relates to an overvoltage protection element provided as a component of a medical device for use on or in a human or animal body.

BACKGROUND OF THE INVENTION

In the following discussion, it is largely assumed that the medical device is provided for use on or in a human or animal body, and accordingly has at least one interface via which the device either outputs signals at a predetermined body location or records them therefrom. The identified interface does not have to be a body-device interface, but rather may also relate to (for example) a terminal of the medical device which may be connected to further measuring or active devices.

Medical devices, in particular electrostimulators (and especially cardiac pacemakers) are currently receiving ever greater attention because of their life-saving and life-sustaining properties. Many medical devices may take over complex physical functions of patients, or support them by appropriately conditioned electrical signals which charge/energize particular body parts. Furthermore, medical devices are often used for the purpose of recording electrical signals from a patient's body and using them for diagnosis or for therapy methods after corresponding processing. Modern medical devices frequently have therapeutic and diagnostic functions, as is the case for modern cardiac pacemakers, for example, which monitor the cardiac muscle activity using special measuring devices adapted for this purpose, and which may also control the muscle activity.

Medical devices of this type share the feature that they have a body-device interface through which they are in contact with a human or animal body for electrical signal transmission. Comparable body-device interfaces are also provided, for example, in external and implantable defibrillators; stimulation configurations for stimulating the auditory nerve; or other implantable measuring and transmission configurations for intracorporeal detection and analysis and/or external transmission of measured values of physiological variables.

If multiple medical devices of this type are used simultaneously in a patient, the danger exists of mutual electrical influence of the functional capability of the devices, which may possibly cause interference or damage to components contained therein by electrical overvoltages. This may occur, for example, if an electrical voltage of a first medical device is coupled via the body of the patient into a body-device interface of a second medical device. If the coupled-in voltage signals result from relatively high voltages applied to the body, as may be output by defibrillators or HF-surgical devices (for example), a second medical device's internal electronic components may be destroyed if the components to which high voltage is applied do not have a suitable dielectric strength.

To avoid internal overvoltages by external coupling, many electrotechnical devices use overvoltage protection circuits, which allow overvoltages coupled into an interface to be reduced to a predetermined minimal value and thus electronic components to be protected from exceedingly high voltage differences and the resulting destruction from electrical voltage breakdown. Overvoltage protection circuits of this type have already proven themselves for decades in many applications in electronic circuitry technology.

A typical overvoltage protection circuit in an input stage of a device, for example, includes a series circuit made of a resistor and a Zener diode, in which the coupled-in overvoltage energy is converted into thermal energy.

A further example of an overvoltage protection circuit, which includes a voltage limiting element provided between two line inputs of an electronic circuit to be protected, and also a current limiting device connected in series to the voltage limiting element, is disclosed in U.S. Pat. No. 5,751,531 A. The current limiting device may be implemented as a MOS transistor, whose gate and source terminals are short-circuited with one another and is only interconnected via its source and drain terminals. The voltage limiting element is typically implemented as a Zener diode.

A similar overvoltage protection circuit, which includes two 60 V Zener diodes connected to one another in a reverse direction, and connected between an input terminal and a ground terminal, is disclosed in U.S. Pat. No. 4,661,979. Furthermore, this overvoltage protection circuit includes two diodes connected to one another in the reverse direction inside an integrated circuit, which are provided between the two inputs of the integrated circuit and an internal ground terminal, and a diode connected in the forward direction, which is connected between the internal ground terminal and a voltage supply.

Known overvoltage protection circuits described above allow the implementation of a short-circuit upon application of an overvoltage signal, via which the high voltages and energies, which possibly result in damage to further electronic components, may be dissipated.

However, if a defibrillator is used on a body provided with further body-device interfaces of a medical device, the implementation of a shunt circuit in the medical devices to be protected would have the result that the defibrillation energy is not completely active on the heart of the patient, but rather would be dissipated from the body of the patient via the short-circuit and would thus be lost for the defibrillation. This is particularly the case if the body-device interface is situated in proximity to the body region to which the defibrillation energy is applied, as is the case with stimulators and cardiac pacemakers.

It is therefore desirable for the energy output during defibrillation via the defibrillator electrodes to act substantially completely on the body of the patient and not be dissipated unused via a body-device interface of a further medical device.

SUMMARY OF THE INVENTION

The present invention seeks to provide an overvoltage protection element as a component of a medical device intended for use on or in a human or animal body, which avoids the described disadvantages of the overvoltage protection circuits known from the prior art.

The invention is based on the idea of providing reshaping means in an overvoltage protection element, which are implemented for the purpose of converting external overvoltage signals at an interface of a medical device into at least one internal voltage pulse. In this way, a direct voltage short-circuit is avoided over the duration of the external overvoltage signal by a suitable selection of the reshaping means, wherein the entire amount of energy coupled into the medical device integrated over the chronological duration of the external overvoltage signal may be reduced in such a way that it does not damage further electronic components of the medical device connected to the overvoltage protection element.

For this purpose, the interface of the medical device may be identical to the body-device interface already identified, or may also be implemented as a further interface of a medical device. In particular, this interface may be a patient terminal of a medical device, which is provided for connecting electrodes of a stimulator or a cardiac pacemaker.

Furthermore, the overvoltage protection element according to the invention provides limiting means, which are provided for the purpose of limiting a voltage drop on at least one electronic component of the medical device to a predetermined limiting value. The remaining voltage load may be adapted to the dielectric strength of the electronic components in the medical device. Such an adaptation prevents damage or impairment of the electronic components. This voltage limiting opens up possibilities for the desired improvements in relation to typical protective circuits, which are solely based on causing an electrical shunt circuit upon the occurrence of overvoltages.

A first version of the invention provides that the reshaping means are connected in series upstream from the limiting means in relation to the propagation direction of the overvoltage signal at the interface.

In a further expedient and cost effective version, the reshaping means include at least one high-voltage-proof capacitor. If an external overvoltage signal having chronological rising and/or decay characteristic is applied to the capacitor, the capacitor is put into a charge state and a following discharge state, with DC voltage components of the external voltage signal being filtered out and only an internal pulse being able to be coupled into the overvoltage protection element. If the external overvoltage signal is a chronologically brief defibrillation pulse, this also results in short-term charging and discharging of the capacitor.

Through suitable dimensioning of the capacitor, the time characteristic of the coupled-in voltage pulse and the level of the coupled-in voltage may be predetermined. As a result, the provision of an appropriately dimensioned capacitor allows adaptation of both the chronological conversion and also the energetic conversion of the external voltage signal. However, it must be ensured that the capacitor does not impair the signal decoupling or signal coupling of the useful signals of the medical device. Through suitable dimensioning of the capacitor, the energy quantity and energy density coupled into the medical device may be influenced, but chronologically changing useful signals—such as stimulation pulses of a cardiac pacemaker—may be decoupled largely without resistance via the interface. A capacitor thus provides an efficient overvoltage protector without impairing the functionality of the medical device.

In a further version, it is provided that the limiting means become essentially current-conducting at low impedance above a predetermined absolute voltage value, and implement an input-side electrical connection path for a compensation of the voltages applied to further electronic components of the medical device.

In this case, "applied voltages" refers to a voltage difference established by the circuit construction and/or the interconnection of the further components of the medical device. Thus, for example, by changing a potential value, even if the absolute voltage amount of the internal voltage pulse remains the same, the level of the relative voltage amplitudes, i.e., the level of the voltage difference which may be applied to further components of the medical device, varies. By implementing an input-side electrical connection path, the voltage drop on electronic components provided in the medical device may be influenced in such a way that no damaging potential differences occur, which could possibly cause a voltage breakdown in the components. The electrical connection path may allow a compensation of potentials applied to the components of the medical device and thus avoids damaging potential differences.

In a further version of the overvoltage protection element, the limiting means become essentially low-impedance current conducting if a voltage is applied whose absolute value exceeds a predetermined absolute value of a useful voltage, in particular a maximum output voltage or measuring voltage of the medical device, and form an input-side electrical current path for a compensation of the voltages applied to further electronic components of the medical device. As a result, it may be ensured that no shunt circuit occurs through the limiting means as long as the medical device is used regularly.

The limiting means may be selected in accordance with the useful voltage of the medical device so that all useful voltages lie below a threshold at which the limiting means become essentially current conducting. For all higher voltages, in particular coupled-in external overvoltage signals, the limiting means become essentially current conducting, which prevents damage to electronic components of the medical device by potential compensation. In other versions of the limiting means, the voltage threshold may also lie above the highest useful voltage absolute value occurring in regular operation by a predetermined absolute value, in order to ensure additional security upon the occurrence of unexpected voltage oscillations. A typical threshold value of a cardiac pacemaker having an overvoltage protection element according to this version of the invention might be in the range of 10 V to 20 V, for example.

In another version of the overvoltage protection element, the limiting means may include at least one voltage limiting circuit which is symmetrical in regard to its configuration. Because of the symmetry, easier dimensioning of the components of the voltage limiting circuit is made possible because typically only a part of the circuit has to be dimensioned in their configuration. Furthermore, no consideration of the polarity of the terminals is required in the interface of the medical device because no electrical preferential orientations exist in regard to the voltage pulses coupled into the overvoltage protection element. The limiting means may thus also be independent of the voltage polarity, and the functional capability of the limiting means may be ensured for both positive and also negative overvoltage signals.

In a further version, the limiting means may include at least two Zener diodes which are connected in parallel to the interface and in series to one another, one Zener diode being connected in the blocking direction and one in the transmitting direction. Zener diodes typically behave like normal diodes in the transmitting direction, but in the blocking direction they become low-impedance conductive above a predetermined voltage (the breakdown voltage). Accordingly, Zener diodes are suitable for representing voltage limiting circuits which change their conduction behavior at a predetermined voltage limiting value, and may thus influence current flow and voltage drop in a circuit for voltage limiting purposes.

By providing two Zener diodes connected to one another in series, one of which is connected in the transmitting direction and the other in the blocking direction, the voltage polarity of a coupled-in internal voltage pulse becomes unimportant. While one of the two Zener diodes may block negative internal voltage pulses below a breakdown voltage value, and only oppose positive internal voltage pulses of a predetermined absolute value with a slight conduction resistance, the other Zener diode accordingly behaves in reverse in relation to the polarity of the internal voltage pulse. As a result, it is ensured that above the absolute value of a breakdown voltage value, both Zener diodes become low-impedance conductive, but one Zener diode is blocking below this breakdown voltage value. The voltage limiting may be achieved above a breakdown voltage value by implementing an electrical connection path to compensate for the voltages applied to further electronic components of the medical device.

In a further version, it is provided that the high-voltage-proof capacitor or capacitors each have a capacitance of less than 200 µF, in particular less than 100 µF, and preferably less than 50 µF. The designated capacitances are well suited for the extensively non-resistant output of predetermined voltage pulses of a useful voltage in stimulators and cardiac pacemakers.

In a further version of the present invention, it is provided that the interface of the medical device is a bipolar interface and each pole of this interface is terminated using an overvoltage-proof capacitor. Bipolar interfaces are typically used in stimulators and cardiac pacemakers. As a result of each pole of the interface terminating in a sufficiently voltage-proof capacitor, when external voltage signals having equal chronological rising and/or decay characteristics are applied (as in the case of a typical defibrillation application, for example), an internal voltage pulse is generated which has an extensively equal time behavior for both poles. Furthermore, it is ensured that each overvoltage signal coupled into the bipolar interface is converted into an internal voltage pulse.

In addition, a further version of the invention may provide that the limiting means include at least one switch which is transferred into a closed position by a threshold value discriminator if a predetermined voltage absolute value of the internal voltage pulse(s) is exceeded. An electrical connection path is therefore created to compensate for the voltages applied to further electronic components of the medical device. A corresponding overvoltage protection element may thus be implemented in multiple parts using simple electronic switching means employing threshold value discriminators known from the prior art.

DETAILED DESCRIPTION OF PREFERRED VERSIONS OF THE INVENTION

Figure 1:
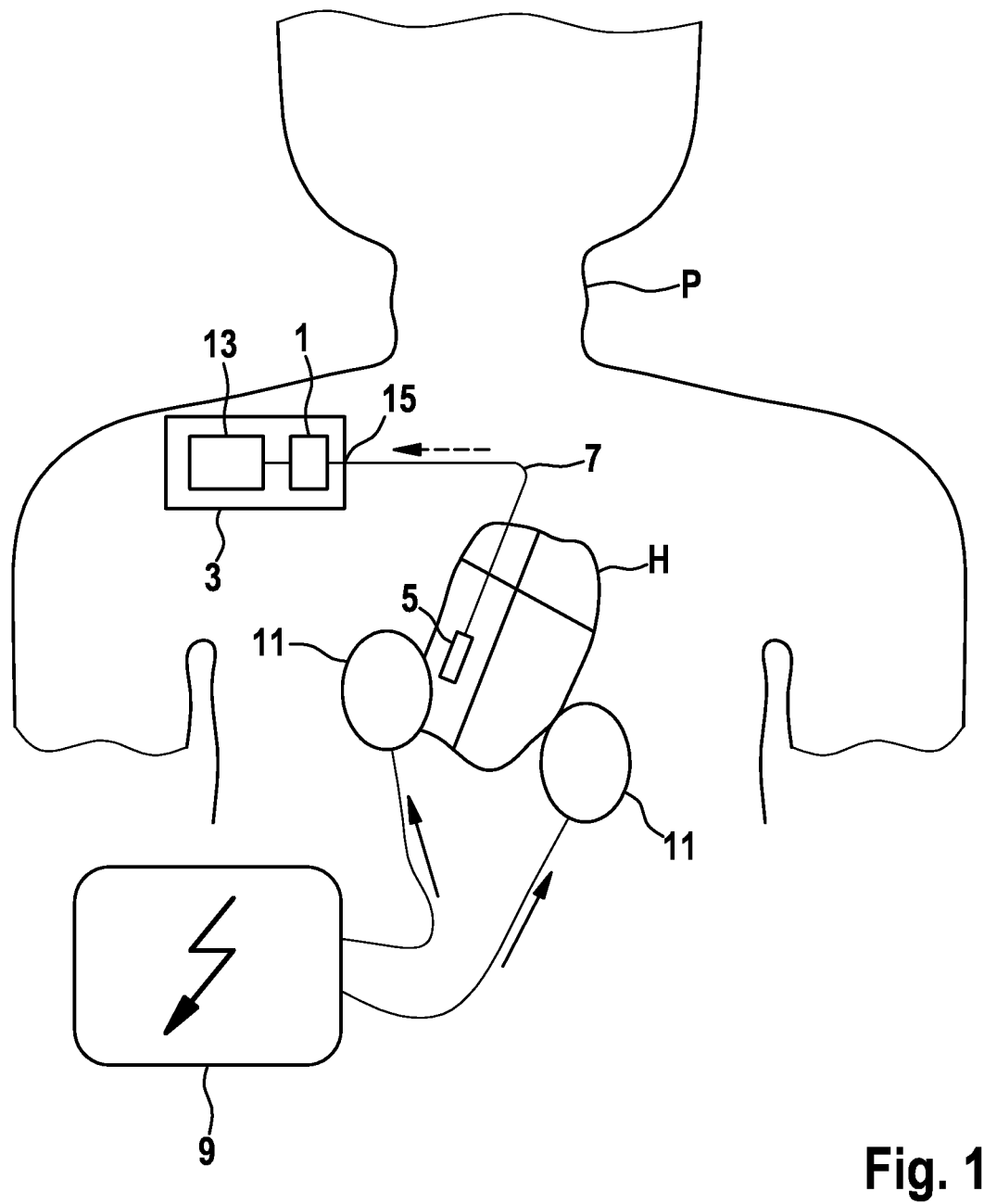
FIG. 1 is a simplified schematic view of an overvoltage protection element 1 provided with an implanted medical device 3.

FIG. 1 shows an overvoltage protection element 1 provided on an implanted cardiac pacemaker 3. The cardiac pacemaker has an interface supply line (electrode line) 7 for the electrical connection to a body-device interface 5, which is implemented here as an electrode inserted into the heart H of the patient P. The electrode (body-device interface) 5 is supplied with voltage pulses generated by the cardiac pacemaker 3 for cardiac muscle stimulation. Alternatively, cardiac signals may also be detected using the body-device interface 5 and conducted via the interface supply line 7 to the cardiac pacemaker. The interface supply line 7 is provided with the overvoltage protection element 1 at the cardiac pacemaker.

Furthermore, FIG. 1 shows an external defibrillator 9, which includes two further body-device interfaces implemented as external defibrillation electrodes 11. If the defibrillator 9 is used on the patient, a voltage pulse is applied to the chest of the patient via the defibrillation electrodes 11. The output of shock pulses is symbolized by two arrows, which lead from the defibrillator 9 to the two defibrillation electrodes 11. Because of the local proximity of the defibrillation electrodes 11 and the electrode 5 of the cardiac pacemaker 3 at the moment of the delivery of the voltage pulse, and the conductivity of the body tissue, a part of the defibrillation energy is coupled via the body-device interface 5 of the cardiac pacemaker into the interface supply line 7 and reaches the overvoltage protection element 1, as illustrated by the dashed arrow. However, because of the action of the overvoltage protection element 1, only a small part of the defibrillation energy is coupled into the cardiac pacemaker 3, thereby protecting the cardiac pacemaker 3.

Figure 2:
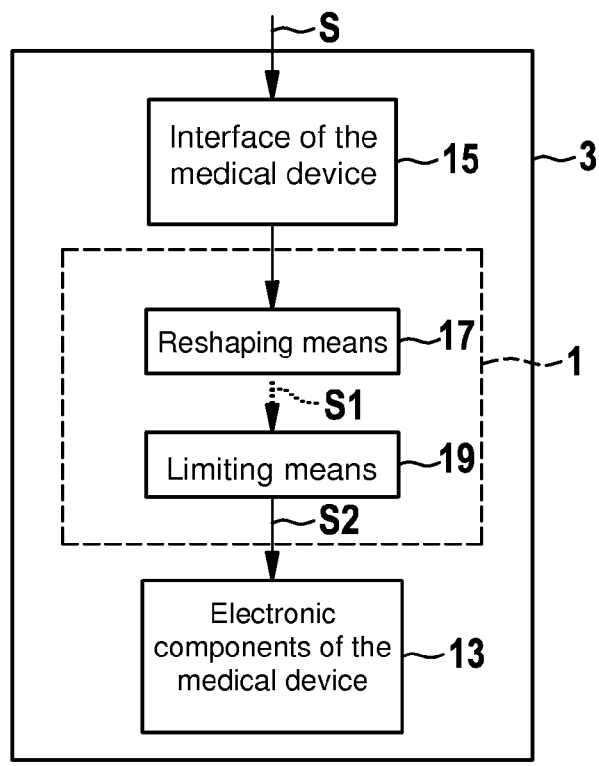
FIG. 2 is a block diagram illustrating the function of the overvoltage protection element 1 for converting an external overvoltage signal in the medical device 3.

FIG. 2 shows a block diagram illustrating the function of the overvoltage protection element 1 for converting an external overvoltage signal in the medical device 3. If an external overvoltage signal S having chronological rising and/or decay characteristics is applied to an interface 15 of the device 3, the signal is first coupled into the interface. Reshaping means 17 of the overvoltage protection element 1 are implemented for the purpose of converting the external overvoltage signal S into an internal voltage pulse S1.

In accordance with the absolute value of the internal voltage pulse S1, limiting means 19 of the overvoltage protection element 1 may limit the relative amplitude of the internal voltage pulse S1, which may be applied to further electronic components 13 of the medical device 3, to a predetermined limiting value S2. In one version, the limiting means 19 become essentially low-impedance current conducting above a predetermined voltage threshold value, and thus generate a current path to compensate for the voltages applied to the electronic components of the device 13 and thus limit the amplitude.

If the amplitude of the internal voltage pulse is below the limiting value defined by the limiting means 19, the limiting means 19 remain in a nonconductive state. The voltage S2 applied to the electronic components 13 corresponds to the absolute value of the amplitude of the internal voltage pulse S1, but does not cause any damage of the electronic components 13, for example, by a voltage breakthrough.

Figure 3:
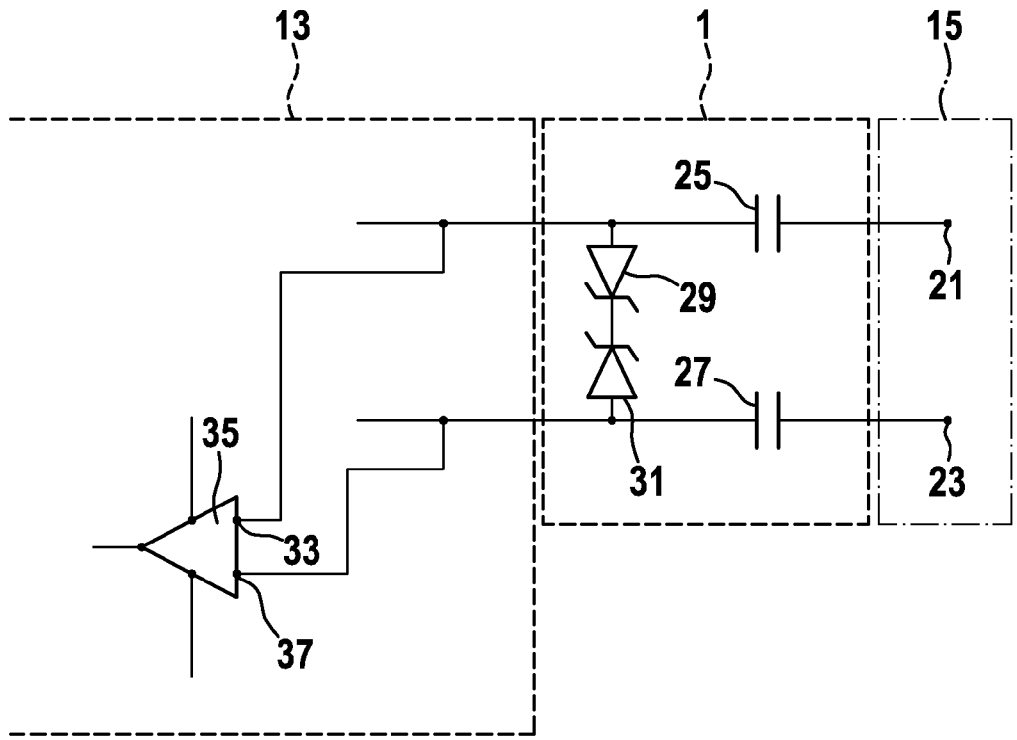
FIG. 3 shows an exemplary version of the overvoltage protection element 1 at the interface 15 of a medical device 3.

FIG. 3 shows an version of the overvoltage protection element 1 at the interface 15 of a medical device 3. The interface 15 is a bipolar interface having a first input 21 and a second input 23. The overvoltage protection element 1 is located at the interface, which has a first capacitor 25 and a second capacitor 27 as the reshaping means connected downstream in series from the inputs 21 and 23. The capacitors are capable of converting an externally applied overvoltage signal having chronological rising and/or decay characteristics into a coupled-in internal voltage pulse. Two Zener diodes 29 and 31 are connected downstream, which are connected in series in opposing polarization and electrically connect both input lines. The capacitor 25 is connected to the first input 33 of the operational amplifier 35, and the capacitor 27 is connected to the second input of the operational amplifier 35. The operational amplifier is to be understood here as only representative of other electronic components 13 which may be provided in the circuit configuration.

If an external voltage is applied to the inputs 21 and 23, having positive potential at input 21, a positive internal voltage pulse is generated by the first capacitor 25. If the absolute value of the internally generated positive voltage pulse is greater than the breakdown voltage of the Zener diode 29, the diode becomes low-impedance conducting. The Zener diode 31 is connected in the flow direction for this positive voltage pulse, so that a current flow occurs via the capacitor 27 to the second input 23. The voltage is thus limited to the sum of the breakdown voltage and flow voltage of the Zener diodes at the terminals 33 and 37 of the operational amplifier. The Zener diodes 29 and 31 are advantageously selected according to their breakdown voltage so that the maximum resulting voltage difference does not cause any damage to the operational amplifier 35.

Furthermore, it is clear to one skilled in the art that if an internal voltage pulse having reversed polarity is coupled in, the functional principle of the present version of the overvoltage protection element 1 is not changed. The two Zener diodes 29 and 31 simply swap their transmitting and blocking properties as a result of the polarity change. As a result, the present configuration of the two Zener diodes 29 and 31 are polarity-independent, symmetrical limiting means.

Figure 4:
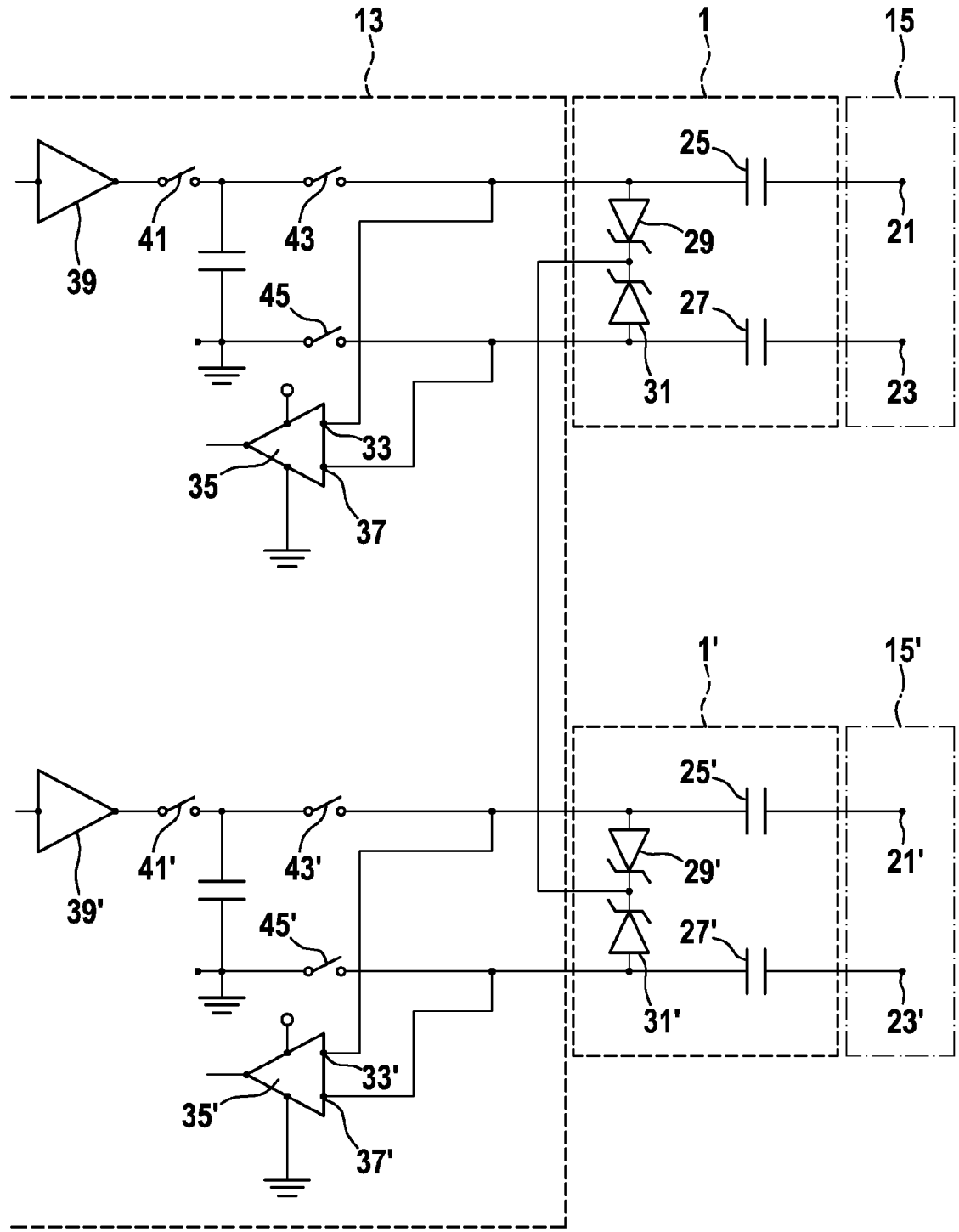
FIG. 4 shows a variation on the arrangement of FIG. 3.

FIG. 4 shows a further version of an overvoltage protection element 1 according to the invention, which is based on the circuit shown in FIG. 3. Notwithstanding that version, however, in the present version two bipolar interfaces 15 and 15' are provided, which are both each terminated by an overvoltage protection element 1 or 1', respectively, which correspond in the fundamental construction to the overvoltage protection element 1 shown in FIG. 3 and therefore do not have to be described once again here.

The two limiting means of the two overvoltage protection elements 1, 1', which each include two Zener diodes 29, 31 or 29', 31', respectively, are connected in the line interconnection shown in the figure in such a way that the conductor sections connecting the particular first Zener diode 29, 29' and the particular second Zener diode 31, 31' are set at an equal potential. As a result, external voltage signals coupled into one of the two overvoltage protection elements are not only compensated for in their potentials via the line sections assigned to one overvoltage protection element 1 or 1', but additionally via the line sections assigned to the two overvoltage protection elements.

In addition to the circuit components described above, the circuit configuration shown in FIG. 4 includes two further amplifier stages 39 and 39', which may be switched in selectively to the individual inputs 21 and 23 or 21' and 23' by a total of six switches 41, 43, and 45 or 41', 43', and 45', respectively. Because the absolute values of the pulse useful signals output by the two amplifier stages 39 and 39' lie below the breakdown voltage of the Zener diodes, they are output via the particular interfaces, which now function as outputs. The two operational amplifiers 35, 35', in contrast, may be used for the measured value amplification of electrical measured signals, which are coupled in via the two interfaces 15, 15'.

The invention is not intended to be limited to the preferred versions of the invention described above, but rather is intended to be limited only by the claims set out below. Thus, the invention encompasses all different versions that fall literally or equivalently within the scope of these claims.

What is claimed is:

1. A medical device for use on or in a body, the medical device including:
   a. one or more electronic components;
   b. an interface supplying the electronic components with input and/or output electrical signals, wherein an external overvoltage signal may be received across the interface,
   c. an overvoltage protection element interposed between the interface and the electronic components, the overvoltage protection element including:
      (1) reshaping means for converting any external overvoltage signal at the interface into a voltage pulse internal to the overvoltage protection element, the reshaping means including a capacitor, and
      (2) limiting means for limiting the amplitude of the voltage pulse from the reshaping means to a predetermined limiting value, wherein the limiting means includes at least two Zener diodes connected:
         (A) in series with one another in cathode-to-cathode relationship, and
         (B) in parallel with the interface.

2. The medical device of claim 1 wherein the reshaping means is interposed between the limiting means and the interface.

3. The medical device of claim 1 wherein the capacitor has a capacitance of less than approximately 200 mF.

4. The medical device of claim 1 wherein:
   a. when the absolute value of the amplitude of the voltage pulse is below a predetermined value, the limiting means is at least substantially nonconductive, and
   b. when the absolute value of the amplitude of the voltage pulse is above the predetermined value, the limiting means:
      (1) is conductive, and
      (2) limits the voltage drop across the limiting means to a predetermined limiting value.

5. The medical device of claim 4 wherein the predetermined value is less than or equal to a maximum input or output voltage of at least one of the electronic components.

6. The medical device of claim 1 wherein the overvoltage protection element is a first overvoltage protection element, the medical device further including a second overvoltage protection element having at least two Zener diodes connected in series with one another, wherein a line extends from a location between the Zener diodes of the first overvoltage protection element to a location between the Zener diodes of the second overvoltage protection element.

7. The medical device of claim 1 wherein the overvoltage protection element includes at least two capacitors, each capacitor being interposed between one of the Zener diodes and the interface.

8. An overvoltage protection element for a medical device used on or in a body, the medical device including an interface at which an external overvoltage signal may be received, the overvoltage protection element including:
   a. reshaping means for converting any external overvoltage signal at the interface into an internal voltage pulse within the overvoltage protection element, the reshaping means including at least one capacitor, and
   b. limiting means for limiting the amplitude of the voltage pulse from the reshaping means to a predetermined limiting value, wherein the limiting means includes at least two Zener diodes connected:
      (1) in parallel with the interface,
      (2) in series with one another, and
      (3) in opposing directions.

9. The overvoltage protection element of claim 8 wherein the reshaping means is connected upstream in series from the limiting means in relation to the direction of propagation of the external overvoltage signal at the interface.

10. The overvoltage protection element of claim 8 wherein each capacitor has a capacitance of less than 200 mF.

11. The overvoltage protection element of claim 8 wherein each capacitor has a capacitance of less than 100 mF.

12. The overvoltage protection element of claim 8 wherein each capacitor has a capacitance of less than 50 mF.

13. The overvoltage protection element of claim 8 wherein:
   a. below an absolute value of a predetermined voltage value, the limiting means is at least substantially nonconductive, and
   b. above the absolute value of the predetermined voltage value, the limiting means defines a low-impedance current conducting electrical path.

14. The overvoltage protection element of claim 8 wherein the limiting means becomes a low-impedance current conducting path if a voltage is applied with an absolute value exceeding an absolute value of a maximum input or output voltage of the medical device.

15. The overvoltage protection element of claim 8 wherein:
   a. the interface of the medical device is a bipolar interface, and
   b. each pole of the interface includes a capacitor.

16. A medical device for use on or in a body, the medical device including:
   a. one or more electronic components;
   b. an interface supplying the electronic components with input and/or output electrical signals, wherein:
      (1) an overvoltage signal may be received across the interface,
      (2) the overvoltage signal being external to the medical device;
   c. an overvoltage protection element interposed between the interface and the electronic components, the overvoltage protection element including:
      (1) a reshaping unit configured to convert external overvoltage signals at the interface into a voltage pulse internal to the overvoltage protection element, the reshaping unit including a capacitor; and
      (2) a limiting unit configured to limit the amplitude of the voltage pulse to a predetermined limiting value, wherein the limiting means includes at least two Zener diodes connected:
         (1) in parallel with the interface,
         (2) in series with one another, and
         (3) in opposing directions.

17. The medical device of claim 16 wherein:
   a. the interface is a bipolar interface having a first input and a second input;
   b. the reshaping unit includes a first capacitor and a second capacitor; and
   c. the first input is in series with the first capacitor, and the second input is in series with the second capacitor.

18. The medical device of claim 16 wherein the anodes of the first and second Zener diodes are connected to the electronic components.

19. A medical device for use on or in a body, the medical device including:
   a. one or more electronic components;
   b. an interface supplying the electronic components with input and/or output electrical signals, wherein:
      (1) the interface is a bipolar interface having a first input and a second input;
      (2) an overvoltage signal may be received across the interface, the overvoltage signal being external to the medical device;
   c. an overvoltage protection element interposed between the interface and the electronic components, the overvoltage protection element including:
      (1) a reshaping unit configured to convert external overvoltage signals at the interface into a voltage pulse internal to the overvoltage protection element, wherein:
         (A) the reshaping unit includes a first capacitor and a second capacitor; and
         (B) the first input is in series with the first capacitor, and the second input is in series with the second capacitor; and
      (2) a limiting unit configured to limit the amplitude of the voltage pulse to a predetermined limiting value, wherein:
         (A) the limiting unit includes a first Zener diode and a second Zener diode, each Zener diode having an anode and a cathode;
         (B) the first and second Zener diodes are connected to each other cathode-to-cathode;
         (C) the first input, the first capacitor, and the anode of the first Zener diode are connected in series; and
         (D) the second input, the second capacitor, and the anode of the second Zener diode are connected in series.

20. A medical device for use on or in a body, the medical device including:
   a. one or more electronic components;
   b. an interface supplying the electronic components with input and/or output electrical signals, wherein:
      (1) the interface is a bipolar interface having a first input and a second input;
      (2) an overvoltage signal may be received across the interface, the overvoltage signal being external to the medical device;
   c. an overvoltage protection element interposed between the interface and the electronic components, the overvoltage protection element including:
      (1) a reshaping unit configured to convert external overvoltage signals at the interface into a voltage pulse internal to the overvoltage protection element, wherein:
         (A) the reshaping unit includes a first capacitor and a second capacitor; and
         (B) the first input is in series with the first capacitor, and the second input is in series with the second capacitor; and
      (2) a limiting unit configured to limit the amplitude of the voltage pulse to a predetermined limiting value, wherein:
         (A) the limiting unit includes a first Zener diode and a second Zener diode, each Zener diode having an anode and a cathode;
         (B) the first and second Zener diodes are connected to each other cathode-to-cathode;
         (C) the first input is directly connected to the first capacitor, and the second input is directly connected to the second capacitor; and
         (D) the first capacitor is directly connected to the anode of the first Zener diode, and the second capacitor is directly connected to the anode of the second Zener diode.

21. A medical device for use on or in a body, the medical device including:
   a. one or more electronic components;
   b. an interface supplying the electronic components with input and/or output electrical signals, wherein:
      (1) the interface is a bipolar interface having a first input and a second input;
      (2) an overvoltage signal may be received across the interface, the overvoltage signal being external to the medical device;

c. a first overvoltage protection element interposed between the interface and the electronic components, the overvoltage protection element including:
   (1) a reshaping unit configured to convert external overvoltage signals at the interface into a voltage pulse internal to the overvoltage protection element, wherein:
      (A) the reshaping unit includes a first capacitor and a second capacitor; and
      (B) the first input is in series with the first capacitor, and the second input is in series with the second capacitor; and
   (2) a limiting unit configured to limit the amplitude of the voltage pulse to a predetermined limiting value; and
d. a second overvoltage protection element, wherein:
   (1) each limiting unit of the first and second overvoltage protection elements includes a first Zener diode and a second Zener diode,
      (A) each Zener diode having an anode and a cathode,
      (B) the Zener diodes of the first overvoltage protection element being connected to each other cathode-to-cathode, and the Zener diodes of the second overvoltage protection element being connected to each other cathode-to-cathode; and
   (2) a connecting line extends from a location between the first and second Zener diodes of the first overvoltage protection element to a location between the first and second Zener diodes of the second overvoltage protection element.

22. A medical device for use on or in a body, the medical device including:
   a. one or more electronic components;
   b. an interface supplying the electronic components with input and/or output electrical signals, wherein:
      (1) the interface is a bipolar interface having a first input and a second input; and
      (2) an overvoltage signal may be received across the first and second inputs of the bipolar interface, the overvoltage signal being external to the medical device;
   c. an overvoltage protection element interposed between the interface and the electronic components, the overvoltage protection element including:
      (1) a reshaping unit configured to convert external overvoltage signals at the interface into a voltage pulse internal to the overvoltage protection element, wherein the reshaping unit includes a first capacitor in series with the first input, and a second capacitor in series with the second input; and
      (2) a limiting unit configured to limit the amplitude of the voltage pulse to a predetermined limiting value, wherein the limiting unit includes a first Zener diode and a second Zener diode, the first and second Zener diodes connected:
         (A) in series with one another in cathode to cathode relationship; and
         (B) in parallel with the interface.

* * * * *